United States Patent [19]
Kallenbach et al.

[11] Patent Number: 5,986,153
[45] Date of Patent: Nov. 16, 1999

[54] OLEFIN COLOR STABILIZATION

[75] Inventors: Lyle R. Kallenbach; Jeffrey W. Freeman, both of Bartlesville, Okla.

[73] Assignee: Phillips Petroleum Company, Bartlesville, Okla.

[21] Appl. No.: 08/941,587

[22] Filed: Sep. 30, 1997

[51] Int. Cl.⁶ ...................................................... C07C 7/20
[52] U.S. Cl. ............................. 585/2; 528/485; 528/491; 528/494
[58] Field of Search ................................ 585/2; 528/485, 528/491, 494

[56] References Cited

U.S. PATENT DOCUMENTS

| | | | |
|---|---|---|---|
| 2,349,904 | 5/1944 | Hachmuth | 585/530 |
| 3,117,167 | 1/1964 | Burch et al. | 568/701 |
| 4,034,061 | 7/1977 | McArthur | 423/213.5 |
| 5,071,539 | 12/1991 | Hayward et al. | 208/114 |
| 5,427,689 | 6/1995 | Kallenbach et al. | 210/670 |
| 5,461,021 | 10/1995 | Kallenbach | 502/202 |
| 5,618,407 | 4/1997 | Kallenbach et al. | 208/114 |

*Primary Examiner*—Walter D. Griffin
*Assistant Examiner*—Nadine Preish
*Attorney, Agent, or Firm*—Lucas K. Shay

[57] ABSTRACT

A process for substantially stabilizing the color of a fluid which comprises an olefin is disclosed. The process comprises contacting the fluid with a composition, which comprises aluminum, zirconium and a borate, under a condition effective to stabilize the color of the fluid.

6 Claims, No Drawings

OLEFIN COLOR STABILIZATION

FIELD OF THE INVENTION

This invention relates to a process for stabilizing the color of olefins.

BACKGROUND OF THE INVENTION

Olefins are a class of very important chemicals. For example, an α-olefin can be used as a monomer or comonomer to produce an olefin polymer such as polyethylene. Lower olefins such as ethylene and propylene are generally produced by thermal cracking of saturated hydrocarbons. Higher olefins having 6 or more carbon atoms per molecule are generally produced by ethylene oligomerization. One example is the production of 1-hexene by catalytic trimerization of ethylene catalyzed by a composition comprising a chromium compound, a pyrrolide compound, and a metal alkyl. The trimerization process also produces decenes as by-products. Decenes are generally separated from 1-hexene by distillation and can be used as comonomers for producing olefin polymers, as synthetic lubricating oils, as detergents, as intermediates and feedstock for conversion to alcohols, or as solvent.

One problem facing the production of decenes is the association of a pyrrolide compound with the decenes because both the decenes and pyrrolide compounds have about the same or similar boiling point. Olefins containing a pyrrolide compound are subject to discoloration thereby rendering the olefins less attractive or useless. Therefore, it is highly desirable to substantially stabilize the color of an olefin.

SUMMARY OF THE INVENTION

An object of the invention is to provide a process for substantially stabilizing the color of an olefin. Also an object of the invention is to provide a process for substantially removing a color-causing compound contained in an olefin. Another object of the invention is to provide a process for substantially removing a pyrrolide compound from a olefin. An advantage of the invention is that the color of an olefin can be substantially stabilized by the invention process. Other objects or advantages will become more apparent as the application is more fully disclosed hereinbelow.

According to the invention, process which can be used to substantially stabilize the color of an olefin or removing a pyrrolide compound is provided. The process comprises contacting a fluid with a composition wherein the fluid comprises an olefin, the composition comprises, consists essentially of, or consists of aluminum, zirconium, and boron, and the process is carried out under a condition sufficient to substantially stabilize the color of the fluid.

DETAILED DESCRIPTION OF THE INVENTION

The term "fluid" used herein refers to gas, vapor, liquid, or combinations of two or more thereof. The term "substantial" or "substantially" refers to more than trivial. The term "stabilized color" refers to a color of an olefin that is substantially unchanged upon storage of the olefin for at least about 30, preferably about 60, and most preferably 90 days under atmospheric pressure at about 20 to about 50° C. The term "stabilizing color" denotes a process for obtaining a stabilized color.

According to the invention, any olefins contaminated with a color-causing or color-forming compound can be employed. Examples of olefins include, but are not limited to, ethylene, propylene, butenes, pentenes, 4-methyl-1-pentene, hexenes, heptenes, octenes, nonenes, decenes, undecenes, dodencenes, pentadecenes, octadecenes, and combinations of two or more thereof. The color-forming compounds can be any compounds that, upon storage, develop color. Generally the color-forming compounds are nitrogen-containing compounds. Examples of color-forming compounds include, but are not limited to pyridines, quinolines, amines, indoles, indolines, hexahydrocarbazoles, pyrrolides, and combinations of any two or more thereof. Examples of pyrrolides include, but are not limited to, hydrogen pyrrolide (pyrrole), lithium pyrrolide, sodium pyrrolide, potassium pyrrolide, cesium pyrrolide, and/or the salts of substituted pyrrolides, because of high reactivity and activity with the other reactants. Examples of substituted pyrrolides include, but are not limited to, pyrrole-2-carboxylic acid, 2-acetylpyrrole, pyrrole-2-carboxaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrroleproprionate, ethyl-3,5-dimethyl-2-pyrrolecarboxylate, and combinations of two or more thereof.

The concentration of an olefin in the fluid can be any concentration so long as the color of the olefin can be stabilized. Generally, olefin concentration in the fluid can be at least about 50%, preferably at least about 80%, more preferably at least about 90%, and most preferably at least 95% by weight. The color-forming compound contaminant in the fluid is preferably less than about 10%, preferably less than about 7%, and most preferably less than 5%. The fluid can also contain certain non-olefinic hydrocarbons, such as alkanes or other fluids such as nitrogen, air, steam, or combinations thereof.

The composition used for substantially stabilizing the color of an olefin or removing the color-forming compounds in an olefin in the invention comprises, consists essentially of, or consists of, aluminum, zirconium, and borate. Aluminum and zirconium in the composition are generally not in the metal form. Preferably the composition comprises, consists essentially of, or consists of aluminum borate and zirconium borate. More preferably the composition comprises, consists essentially of, or consists of a zirconium/aluminum/borate composite.

Generally, the composition has a weight ratio of Al to Zr in the range of from about 0.1:1 to about 30:1, preferably about 1:1 to about 20:1, and most preferably about 4:1 to about 12:1 and a weight ratio of (Al+Zr) to B in the range of from about 0.1:1 to about 10:1, preferably about 1:1 to about 6:1, and most preferably about 1.5:1 to about 3:1. Generally, the composition has a surface area, measured by the BET method employing $N_2$, of about 200 to about 400 $m^2/g$ and a pore volume, measured by a pore size distribution method employing $N_2$, of about 0.2–1.5 cc/g. It can have any suitable shape such as spherical, cylindrical, trilobal or irregular, or combinations of two or more thereof. It also can have any suitable particle size. The presently preferred size is about 0.4 to about 0.8 mm. If particles of the support component have been compacted and extruded, the formed cylindrical extrudates generally have a diameter of about 1 to about 4 mm and a length of about 3 to about 10 mm. It is within the scope of this invention to have minor amounts of aluminum oxide and zirconium oxide, generally about 1 to about 5 weight % of each, present in the composition.

Preferably, the composition is prepared by a method comprising coprecipitation. A first aqueous solution containing any water-soluble, aluminum salt such as, for example, aluminum nitrate; any water-soluble, zirconium salt such as, for example, zirconyl nitrate; and any water-soluble, acidic boron compound (preferably a boric acid, more preferably $H_3BO_3$) is prepared. Any suitable concentrations of these compounds in the aqueous solution can be employed so long as the concentration can result in the production of the composition disclosed above. Generally about 0.02 to about 1 mole/l of each compound, depending on the desired Al:Zr:B ratio can be employed. The initial pH of this aqueous solution is generally about 1 to about 3.

An aqueous alkaline solution, preferably an aqueous solution of ammonia containing about 25 to about 28 weight % $NH_3$, generally having a pH of about 10 to about 14, is then added to the first aqueous solution in an amount sufficient to raise the pH of the first solution to 7 or above 7, preferably to about 8–9, to afford the coprecipitation of borates of aluminum and zirconium.

The dispersion of the formed coprecipitate in the aqueous solution is then subject to any suitable solid-liquid separation methods known to one skilled in the art such as, for example, filtration to substantially separate the coprecipitate from the aqueous solution. Preferably, the coprecipitate is washed with water to remove adhered solution therefrom, optionally followed by washing with a water-soluble organic solvent such as methanol, ethanol, isopropanol, acetone, or combinations of two or more thereof. The presently preferred solvent is isopropanol. The washed coprecipitate is generally dried by any methods known to one skilled in the art. The presently preferred drying is in a vacuum oven, under any pressure, at a temperature of about 110 to about 180° C. for about 2 to about 16 hours.

The dried solid is then calcined by any methods known to one skilled in the art. Generally calcination can be done in air, at a temperature of about 300 to about 1000° C., preferably about 350 to about 750° C., and most preferably 450 to 600° C., for about 1 to about 16 hours. It is within the scope of this invention to mix the formed coprecipitate with a carbon-containing binder material, such as a polyglycol, a polyoxazoline or carbon black, which is substantially burned off during the calcining step, and/or with an inorganic binder material such as, for example, alumina, colloidal alumina, clay, calcium aluminate, water glass or combinations of two or more thereof. It is also within the scope of the invention to extrude or pelletize or tablet the coprecipitate, with or without a binder, before the calcination.

The contacting of a fluid stream comprising an olefin and a color-forming compound in the presence of the aluminum/zirconium/boron composition can be carried out in any technically suitable manner, in a batch, semicontinuous, or continuous process under any effective condition for substantially stabilizing the color of the olefin. Generally, a fluid stream containing an olefin and a color-forming compound is introduced into a suitable vessel or reactor in a fixed catalyst bed, or a moving catalyst bed, or a fluidized catalyst bed, or combinations of any two or more thereof by any means known to one skilled in the art such as, for example, pressure, meter pump, and other similar means. The catalyst bed contains the composition disclosed above. The condition can include a weight hourly space velocity (WHSV) of the olefin fluid stream in the range of from about 0.01 to about 100, preferably about 0.05 to about 50, and most preferably 0.1 to 30 g feed/g composition/hour. Generally, the pressure can be in the range of from about 0 to about 1000 psig, preferably about 20 to about 750 psig, and most preferably 50 to 600 psig, and the temperature is about 10 to about 500° C., preferably about 20 to about 300° C., and most preferably 30 to 200° C.

The product stream or process effluent generally contains an olefin or a mixture of olefins having stabilized color. The composition can be regenerated to its original color—stabilizing activity by any methods known to one skilled in the art. One of the methods is to subject the composition to a stream of air or oxygen-containing fluid at about the same temperature employed in the color-stabilizing process of the invention. Another method is to calcine the used composition at a temperature in the range of from about 200° to about 1500° C., preferably about 300° to about 1000° C., and most preferably 400° C. to 750° C.; for about 30 minutes to about 15 hours; and under a pressure that can accommodate the temperature range disclosed above.

In a preferred embodiment, the process of the invention is suitable for substantially removing a pyrrolide from a fluid comprising decenes. Decenes are produced in the oligomerization of ethylene which is disclosed hereinbelow. The term "oligomerization", unless otherwise indicated, includes dimerization, trimerization, tetramerization, pentamerization, or any process that an olefin self-reacts to form a new olefin having a larger molecule than the original olefin. Oligomerization can also used to denote co-oligomerization in which olefin reacts with a second olefin to give rise to a larger molecule olefin.

Catalysts useful in the oligomerization of ethylene comprise a chromium source, a pyrrolide compound, and a metal alkyl, all of which have been contacted and/or reacted in the presence of an unsaturated hydrocarbon such as, for example, 1-hexene. Optionally, these catalysts can be supported on an inorganic oxide support. These catalysts are especially useful for the oligomerization of olefins, such as, for example, ethylene to 1-hexene.

The chromium source can be one or more organic or inorganic compounds, wherein the chromium oxidation state is from 0 to 6. Generally, the chromium source will have a formula of $CrX_n$, wherein X can be the same or different and can be any organic or inorganic radical, and n is an integer from 1 to 6. Examples include organic radicals having form about 1 to about 20 carbon atoms per radical. Examples of organic radicals include alkyl, alkoxy, ester, ketone, and/or amido radicals. The organic radicals can be straight-chained or branched, cyclic or acyclic, aromatic or aliphatic and can be made of mixed aliphatic, aromatic, and/or cycloaliphatic groups. Examples of inorganic radicals include, but are not limited to halides, sulfates, and/or oxides.

Preferably, the chromium source is a chromium (II)- and/or chromium(III)-containing compound which can yield a catalyst with improved trimerization activity. Examples of chromium compounds include, but are not limited to, chromium carboxylates, chromium napththenates, chromium halides, chromium pyrrolides, and/or chromium dionates. Specific exemplary chromium compounds include, but are not limited to chromium 2,2,6,6-tetramethylheptanedionate, chromium 2-ethylhexanoate (or chromium tris(2-ethylhexanoate), chromium naphthenate, chromium chloride, chromic bromide, chromic fluoride, chromium acetylacetonate, chromium acetate, chromium butyrate, chromium neopentanoate, chromium laurate, chromium stearate, chromium pyrrolides, and/or chromium oxalate.

The pyrrolide compound can be any pyrrolides that will react with a chromium source to form a chromium pyrrolide complex. As used in this disclosure, the term "pyrrolide" refers to hydrogen pyrrolide, i.e., pyrrole ($C_4H_5N$), derivatives of hydrogen pyrrolide, substituted pyrrolides, as well as metal pyrrolide complexes, A "pyrrolide" is defined as a compound comprising a 5-membered, nitrogen-containing heterocycle, such as for example, pyrrole, derivatives of pyrrole, and mixtures thereof.

Examples of pyrrolides include, but are not limited to, hydrogen pyrrolide (pyrrole), lithium pyrrolide, sodium pyrrolide, potassium pyrrolide, cesium pyrrolide, substituted pyrrolides or salts thereof. Examples of substituted pyrrolides includes, but are not limited to, pyrrole-2-carboxylic acid, 2-acetylpyrrole, pyrrole-2-carboxaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrroleproprionate, ethyl-3,5-dimethyl-2-pyrrolecarboxylate, and combinations of two or more thereof. When the pyrrolide contains chromium, the resultant chromium compound can be called a chromium pyrrolide.

The metal alkyl can be any heteroleptic or homoleptic metal alkyl compound. One or more metal alkyls can be used. The alkyl ligand(s) on the metal can be aliphatic and/or aromatic. Preferably, the alkyl ligand(s) are any saturated or unsaturated aliphatic radical. The metal alkyl can have any number of carbon atoms and usually comprises less than about 70 carbon atoms per metal alkyl molecule and preferably less than about 20 carbon atoms per molecule. Examples of metal alkyls include, but are not limited to, alkylaluminum compounds, alkylboron compounds, alkylmagnesium compounds, alkylzinc compounds, alkyllithium compounds, and combinations of two or more thereof. Examples of metal alkyls include, but are not limited to, n-butyllithium, s-butyllithium, t-butyllithium, diethylmagnesium, diethylzinc, triethylaluminum, trimethylaluminum, triisobutylaluminum, triethylaluminum, tripropylaluminum, tributylaluminum, diethylaluminum chloride, diethylaluminum bromide, diethylaluminum ethoxide, diethylaluminum phenoxide, ethylaluminum dichloride, ethylaluminum sesquichloride, and combinations of two or more thereof.

Usually, contacting and/or reacting of a chromium source, a pyrrolide compound and a metal alkyl is carried out in an unsaturated hydrocarbon. The unsaturated hydrocarbon can be any aromatic or aliphatic hydrocarbon, in a gas, liquid or solid state, preferably exemplary unsaturated, aliphatic hydrocarbon compounds include, but are not limited to, ethylene, 1-hexene, 1,3-butadiene, and combinations of two or more thereof. The most preferred unsaturated aliphatic hydrocarbon compound is 1-hexene, because of elimination of catalyst preparation steps and 1-hexene can be a reaction product in ethylene oligomerization. Examples of unsaturated aromatic hydrocarbons include, but are not limited to, toluene, benzene, xylene, mesitylene, hexamethylbenzene, and combinations of two or more thereof. The most preferred unsaturated aromatic hydrocarbon is toluene.

The reaction mixture comprising a chromium source, pyrrolide compound, metal alkyl and unsaturated hydrocarbon can contain additional components which do not adversely affect and can enhance the resultant catalyst system.

Reactants applicable for use in the oligomerization process are olefinic compounds which can (a) self-react, i.e., oligomerize, to give useful products such as, for example, the self reaction of ethylene can give 1-hexene and the self-reaction of 1,3-butadiene can give 1,5-cyclooctadiene; and/or (b) react with other olefinic compounds, i.e., co-oligomerize, to give useful products such as, for example, co-trimerization of ethylene plus hexene can give 1-decene and/or 1-tetradecene, co-trimerization of ethylene and 1-butene can give 1-octene, co-trimerization of 1-decene and ethylene can give 1-tetradecene and/or 1-docosene. For example, the number of olefin bonds in the combination of three ethylene units is reduced by two, to one olefin bond, in 1-hexene. In other example, the number of olefin bonds in the combination of two 1,3-butadiene units, is reduced by two, to two olefin bonds in 1,5-cyclooctadiene. As used herein, the term "oligomerization" is intended to include dimerization and trimerization of diolefins.

Suitable oligomerizable olefin compounds include, but are not limited to, acyclic and cyclic olefins such as, for example, ethylene, propylenes, butenes, pentenes, hexenes, heptenes, octenes, nonenes, diolefins illustrated above, and combinations of two or more thereof.

The oligomerization reaction products can be produced by solution reaction, slurry reaction, and/or gas phase reaction techniques using conventional equipment and contacting processes. Contacting of the monomer or monomers with a catalyst system can be effected by any manner known in the art. One convenient method is to suspend the catalyst in an organic medium and to agitate the mixture to maintain the catalyst system in solution or suspension throughout the oligomerization process. Other known contacting methods can also be employed.

The oligomerization reaction temperatures and pressures can be any temperature and pressure which can trimerize the olefin reactants. Generally, reaction temperatures are within a range of about 0 to about 250° C. Preferably, reaction temperatures within a range of about 60 to about 200° C., and most preferably within a range of 80 to 150° C. are employed. Generally, reaction pressures are within a range of about atmospheric to about 2500 psig. Preferably, reaction pressure within a range of about atmospheric to about 1000 psi and most preferably, within a range of 300 to 700 psi are employed.

The following examples are provided to further illustrate the invention and are not to be construed as to unduly limit the scope of the invention.

EXAMPLE I

This example illustrates the production of decenes and the color of the decenes. The 1-hexene trimerization catalyst and its use in the production of 1-hexene was substantially the same as those disclosed in U.S. Pat. No. 5,376,612 issued Dec. 27, 1994, disclosure of which is incorporated herein by reference, with the exception that a continuous process was employed herein. The catalyst system disclosed in the aforementioned patent was used in a continuous feed reactor system to produce a product stream containing ethylene, 1-hexene, process solvent, mixed olefins and spent catalyst. The process stream was distilled into the following fractions; ethylene, hexenes, process solvent, and mixed olefins. The spent catalyst was left in the kettle along with miscellaneous heavier olefins.

The mixed olefin stream was composed primarily of assorted, mostly branched decenes. The alcohol used to deactivate the catalyst was the next major component. Analyses of representative samples of the mixed olefin stream are given in Table 1.

TABLE 1

Composition of Mixed Olefin Stream

| Component | Sample 1, wt % | Sample 2, wt % | Sample 3, wt % |
| --- | --- | --- | --- |
| Process Solvent[a] | 8.0 | 0.1 | 0 |
| Catalyst Solvent[b] | 1.5 | 0.5 | 0 |
| Alkyl pyrrole[c] | 0.15 | ND | ND |
| Octenes | 2.5 | 0.3 | 0 |
| Mixed Decenes | 65.2 | 79.0 | 80.6 |
| Alcohol[d] | 15.3 | 10.8 | 10.5 |
| Dodecenes | 1.6 | 1.7 | 1.4 |
| Mixed Heavier[e] | 4.1 | 5.5 | 6.1 |
|  | 1.5 | 2.1 | 1.2 |

[a]Methylcyclohexane
[b]The catalyst solvent for sample 1 was toluene and that for samples 2 and 3 was ethylbenzene.
[c]2,5-dimethylpyrrole
[d]The alcohol used to deactivate catalyst was 2-ethyl-1-hexanol.
[e]The heavies were undetermined olefins larger than tetradodecenes.

As seen in Table 1, the amounts of alcohol and alkyl pyrrole in the samples varied. The variability came about because of changes in the process conditions, which in turn affected catalyst usage. In general, the amount of alcohol in the mixed olefin product was not expected to exceed 20% and the amount of alkyl pyrrole was not expected to exceed 0.20%.

A five gallon portion of mixed olefin material from sample 1 was further purified by distillation under nitrogen at 100 torr using standard distillation techniques to give three gallons of a product with the composition given in Table 2 as distillation 1. The product (distillation 1) was distilled a second time under the same conditions in the presence of 30 ml of 93% triethylaluminum to remove the alcohol. A one gallon portion of dodecane was added to the sample to provide for adequate kettle bottom material. The product obtained from this distillation is listed in Table 2 as distillation 2.

TABLE 2

Isolation of Mixed Decenes from the Mixed Olefin Stream

| Component[a] | Distillation 1 | Distillation 2 |
| --- | --- | --- |
| Process Solvent | 0.17 | 0.08 |
| Catalyst Solvent | 0.05 | 0 |
| Alkyl pyrrole | 0.07 | 0.008 |
| Octenes | 0.37 | 0.13 |
| Mixed Decenes | 98.16 | 99.51 |
| Alcohol | 1.12 | 0 |
| Dodecane | 0 | 0.33 |

[a]See footnotes in Table 1.

The presence of the alkyl pyrrole in the mixed decene stream was known to form highly colored decomposition products such as, for example, pyrrole red or pyrrole orange in the presence of air. The addition of acid is also known to catalyze the formation of these highly colored materials. The presence of the alkyl pyrrole in all of the mixed olefin/mixed decene products was evident by the change in color in these products when exposed to air. These changes are listed in Table 3.

TABLE 3

Color Formation in the Mixed Olefin Products[a]

| Product | Initial Color | Color 24 hrs. after air exposure |
| --- | --- | --- |
| Sample 1 | Colorless | Reddish Orange |
| Distillation 1 | Colorless | Orange |
| Distillation 2 | Colorless | Light Yellow |

[a]The color was visually observed or determined.

The color of the samples continued to darken with time and air exposure.

The formation of color in the mixed decene product is known to greatly impact its value as possible solvent, detergent or synthetic lubricant feedstocks since color is not a desirable feature in these products. The difficulty of removing the alkyl pyrrole by distillation demonstrated the need for an alternative method for its removal.

EXAMPLE II

This example illustrates the production of the sorbent composition.

The aluminum/zirconium borate catalyst composition was prepared as follows: 13.2 grams (0.05 mole) of $ZrO(NO_3)_2 \cdot 2H_2O$ (formula weight: 267) and 221.1 grams (0.59 mole) of $Al(NO_3)_3 \cdot 9H_2O$ (formula weight: 375) were mixed with 40.0 grams (0.65 mole) of $H_3BO_3$ (boric acid; formula weight: 62) and 1.0 liter of distilled water. The mixture was heated and stirred until all solids were dissolved.

Thereafter, concentrated aqueous ammonia was added to the entire mixture, which had a pH of about 2, until the pH rose to 8.4 and an Al—Zr-borate coprecipitate was formed. The filter cake was washed with about 1.5 liter of distilled water and then with 1.5 liter of isopropanol. The solid filter cake was dried at 150° C. for about 16 hours (overnight) in a vacuum oven, followed by calcining in air at 500° C. for 4 hours. The calcined Al—Zr borate material (total 89.8 g) had a surface area, measured by the BET method using $N_2$ of 343 $m^2/g$ and a pore volume, measured by a $N_2$ pore size distribution method, of 0.5 $cm^3/g$. It contained 30.0 weight % Al, 8.4 weight % Zr and 11.0 weight % B (boron).

EXAMPLE III

This example illustrates the use of the composition described in Example II in the removal of color-forming compound in a fluid containing decenes produced in Example I.

A stainless steel reactor tube (inner diameter 1.25 centimeter; length 43 centimeters) was filled with a 15 centimeter bottom layer of 3 ml glass beads (inert), 8.5 grams of the composition produced in Example II in the middle 13 centimeter of the tube, and a 15 centimeter top layer of 36 grit alundum (inert). The liquid feed contained a mixture of decenes and 951 parts per million by weight (ppmw) of 2,5-dimethylpyrrol and was produced as described in Example I (sample 1). The feed was introduced into the reactor at a rate of 30 ml/hour. The reactor temperature was 50° C. and pressure was 120 psig. The reactor effluent (product) was collected and analyzed as described below.

A mixed decene feed sample containing 951 ppm 2,5-dimethylpyrrole (DMP) and the reactor effluent product obtained above were analyzed by the method described in ASTM 1492 for bromine number. No change in bromine number between the two samples was detected which indicated little or no change of olefin content. The small amount of DMP expected to be removed by the invention process was not detectable by this method.

The product was then stored at 23° C. for 60 days. Thereafter the DMP content was measured by UV spectyroscopy using 1-decene as a reference standard and 280 nm as the wavelength of measurement. The untreated feed was bright yellow (951 ppm of DMP) while the treated product was clear and had less than 36 ppm DMP which was the detection limit.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed is:

1. A process for substantially removing a color-forming compound selected from the group consisting of pyrrole, lithium pyrrolide, sodium pyrrolide, potassium pyrrolide, cesium pyrrolide, pyrrole-2-carboxylic acid, 2-acetylpyrrole, pyrrole-2-carboxaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrroleproprionate, ethyl-3,5-dimethyl-2-pyrrolecarboxylate, and combinations of two or more thereof from an olefin-containing fluid comprising contacting said olefin-containing fluid with a composition which comprises aluminum, zirconium and a borate wherein said fluid is introduced into contacting with said composition at a rate of about 0.01 to about 100 g of said fluid per g of said composition per hour.

2. A process for substantially removing a color-forming compound selected from the group consisting of 2,5-dimethylpyrrole from an olefin-containing fluid comprising contacting said olefin-containing fluid with a composition which comprises aluminum, zirconium and a borate wherein said fluid is introduced into contacting with said composition at a rate of about 0.01 to about 100 g of said fluid per g of said composition per hour.

3. A process according to claim 1 wherein said olefin is selected for the group consisting of ethylene, propylene, butenes, pentenes, 4-methyl-1-pentene, hexenes, heptenes, octenes, nonenes, decenes, undecenes, dodencenes, pentadecenes, octadecenes, and combinations of two or more thereof.

4. A process according to claim 2 wherein said olefin is a mixture of decenes.

5. A process for stabilizing the color of, and reducing the concentration of a color-forming compound in, a fluid comprising contacting said fluid with a composition wherein said fluid comprises an olefin;

said color-forming compound is 2,5 dimethylpyrrole;

said composition comprises aluminum, zirconium, and borate, and the weight ratio of aluminum to zirconium is 4:1 to about 12:1; the weight ratio of (aluminum+zirconium) to boron is 1.5:1 to about 3:1; and said catalyst composition is a coprecipitate of aluminum borate and zirconium borate; and said fluid is introduced into contacting with said composition at a rate of about 0.01 to about 100 g of said fluid per g of said composition per hour (WHSV).

6. A process according to claim 5 wherein said olefin is a mixture of decenes and the WHSV is 0.1 to 30.

* * * * *